(12) United States Patent
Yan

(10) Patent No.: US 6,240,616 B1
(45) Date of Patent: *Jun. 5, 2001

(54) METHOD OF MANUFACTURING A MEDICATED POROUS METAL PROSTHESIS

(75) Inventor: John Y. Yan, Los Gatos, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/837,993

(22) Filed: Apr. 15, 1997

(51) Int. Cl.[7] .......................................................... B21B 1/46
(52) U.S. Cl. ...................... 29/527.2; 623/1.42; 623/1.46; 623/1.44; 623/1.39; 419/2
(58) Field of Search ................................... 29/527.2, 428; 623/1.42, 1.46, 1.47, 1.48, 1.44, 1.39, 1.4, 1.49, 1.54; 419/2

(56) References Cited

U.S. PATENT DOCUMENTS

| | | |
|---|---|---|
| 3,855,638 | 12/1974 | Pilliar . |
| 4,374,669 | 2/1983 | Mac Gregor . |
| 4,729,871 * | 3/1988 | Morimoto ................................. 419/2 |
| 5,163,958 | 11/1992 | Pinchuk . |
| 5,370,682 * | 12/1994 | Schmitt ................................. 623/1.52 |
| 5,370,684 | 12/1994 | Vallana et al. . |
| 5,437,834 * | 8/1995 | Okimatsu et al. ...................... 419/24 |
| 5,492,768 * | 2/1996 | Okimatsu et al. ...................... 419/24 |
| 5,522,894 | 6/1996 | Draenert . |
| 5,624,411 | 4/1997 | Tuch . |
| 5,630,840 | 5/1997 | Mayer . |
| 5,632,779 | 5/1997 | Davidson . |
| 5,755,771 * | 5/1998 | Penn et al. ........................... 623/1.52 |
| 5,879,398 * | 3/1999 | Swarts et al. ...................... 623/22.21 |
| 5,945,029 * | 8/1999 | Scholz et al. ........................ 264/639 |
| 5,972,027 * | 10/1999 | Johnson ............................... 623/1.52 |

FOREIGN PATENT DOCUMENTS

| | | |
|---|---|---|
| WO 94/13268 | 6/1994 | (WO) . |
| WO 95/11817 | 5/1995 | (WO) . |
| WO 96/28115 | 9/1996 | (WO) . |

OTHER PUBLICATIONS

Lambert, Thomas L., M.D., et al., Localized Arterial Wall Drug Delivery From a Polymer–Coated Removable Metallic Stent, *Circulation*, Eol. 90, No. 2 (Aug. 1994) pp. 1003–1011.

De Scheerder, Ivan K, et al., Biocompatibility of Polymer–Coated Oversized Metallic Stents Implanted in Normal Porcine Coronary Arteries, *Atherosclerosis*, vol. 114 (1995) pp. 105–114.

* cited by examiner

Primary Examiner—S. Thomas Hughes
Assistant Examiner—Marc Jimenez
(74) Attorney, Agent, or Firm—Fulwider Patton Lee & Utecht, LLP

(57) ABSTRACT

A method of manufacturing a medicated prosthesis such as a stent. The method includes forming a stent out of porous metal and loading a therapeutic agent into the pores of the metal. In one embodiment the stent is formed from a sintered metal wire, sheet, or tube and can include adding a coating to the stent. When the stent is implanted into the vasculature of a patient, the therapeutic agent in the stent dissipates into the tissue of the vasculature proximate the stent.

38 Claims, 5 Drawing Sheets

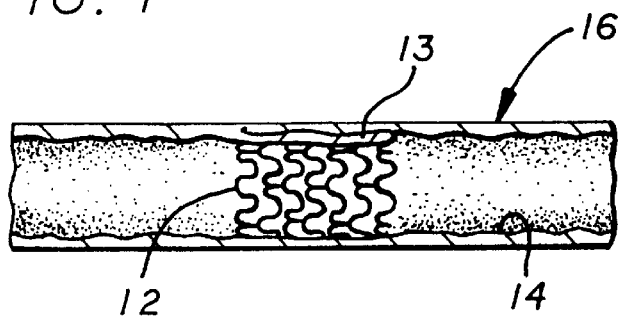
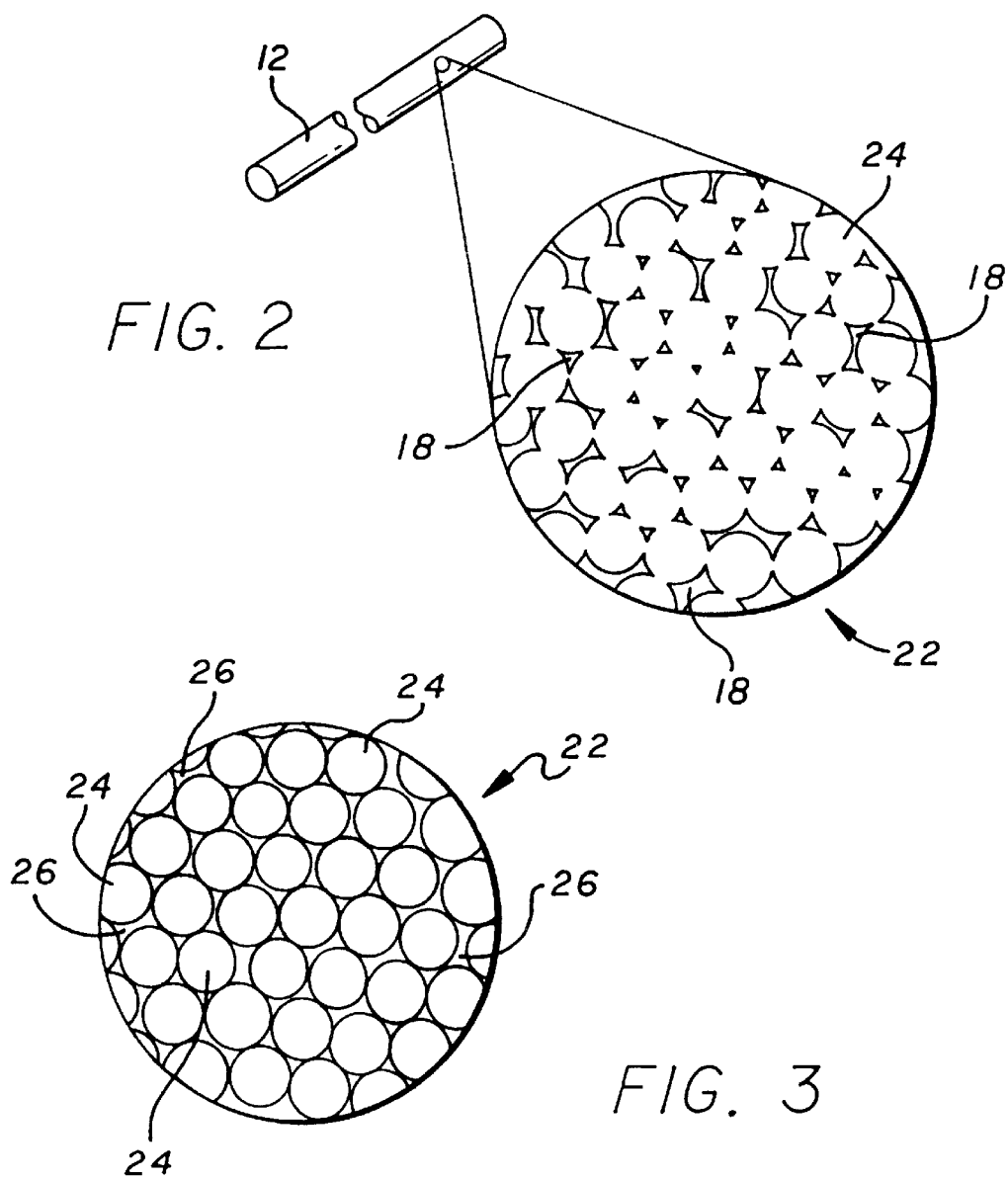

FIG. 9
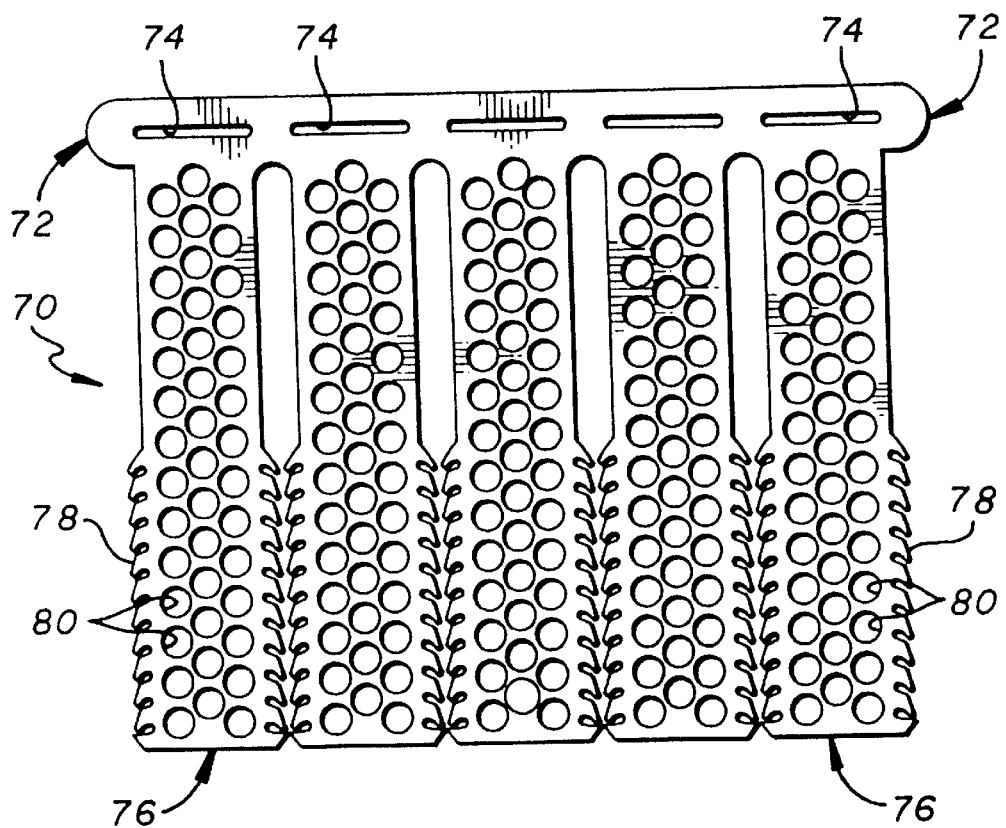
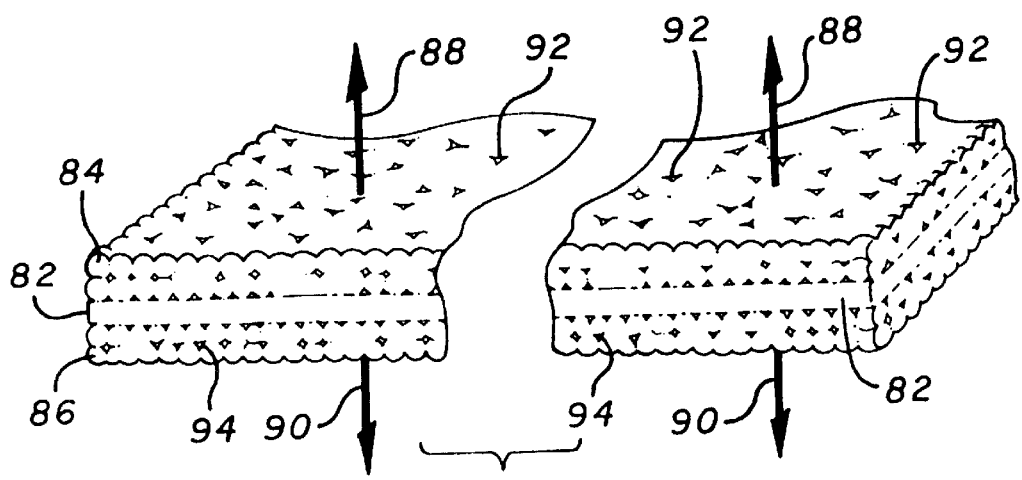
FIG. 10

METHOD OF MANUFACTURING A MEDICATED POROUS METAL PROSTHESIS

BACKGROUND OF THE INVENTION

1. Field of the Invention

This invention generally relates to a medicated prosthesis or implant. More particularly, the invention relates to a medicated intra-vascular prosthesis, such as a stent, that is radially expandable in the vasculature of a patient and delivers a therapeutic agent to the site of the implantation.

2. Description of Related Art

Stents are generally cylindrically shaped prosthetic implants which function to hold open and sometimes expand a segment of a blood vessel or other anatomical lumen. They are particularly suitable for supporting and preventing a torn or injured arterial lining from occluding a fluid passageway. Intravascular stents are increasingly useful for treatment of coronary artery stenoses, and for reducing the likelihood of the development of restenosis or closure after balloon angioplasty.

The success of a stent can be assessed by evaluating a number of factors, such as thrombosis; neointimal hyperplasia, smooth muscle cell migration and proliferation following implantation of the stent; injury to the artery wall; overall loss of luminal patency; stent diameter in vivo; thickness of the stent; and leukocyte adhesion to the luminal lining of stented arteries. However, the chief areas of concern are early subacute thrombosis, and eventual restenosis of the blood vessel due to intimal hyperplasia.

Therapeutic pharmacological agents have been developed to improve successful placement of the stent and are delivered to the site of stent implantation. Stents that are of a common metallic structure were previously unable to deliver localized therapeutic pharmacological agents to a blood vessel at the location being treated with the stent. There are polymeric materials that can be loaded with and release therapeutic agents including drugs or other pharmacological treatments which can be used for drug delivery. However, these polymeric materials may not fulfill the structural and mechanical requirements of a stent, especially when the polymeric materials are loaded with a drug, since drug loading of a polymeric material can significantly reduce the structural and mechanical properties of the polymeric material.

It has been known in the art to coat a metallic stent with a polymeric material and load the polymeric material with a drug. Alternatively stents of polymeric materials have been reinforced with metal structure. These stent designs have the strength necessary to hold open the lumen of the vessel because of the reinforced strength of the metal. Stents made of both polymeric material and metal have a larger radial profile because the volume occupied by the metal portion of the stent cannot absorb and retain drugs. Reducing the profile of a stent is preferable because it increases the in vivo diameter of the lumen created by the stent. Thus it is desirable to configure a metallic stent to deliver drugs to the blood vessel walls without substantially increasing the profile of the stent. The present invention meets these needs.

SUMMARY OF THE INVENTION

Briefly and in general terms, the present invention is a method of manufacturing a medicated prosthesis. The method comprises providing a porous metal material having a plurality of porous cavities, forming the material into a prosthesis having a plurality of porous cavities, and loading therapeutic agents into the pores of the prosthesis. In one embodiment, the prosthesis is a stent for implantation into a blood vessel, biliary duct, esophagus or other body lumen. In one embodiment, the method comprises sintering metal particles including spherical particles, filaments or fibers into a wire, a sheet or tube. Then, the wire, sheet, or tube is further manufactured by forming the stent from the same. Sheets or tubes can be formed into stents by chemical etching or laser cutting the same according to a stent pattern. In another embodiment, the sheet is formed by weaving metallic fibers and sintering the metallic fibers in a metal wire or a sheet.

In yet another embodiment, a sheet of stent material is formed in a plurality of layers. A layer of large diameter particles are arranged in a first horizontal plane. Two layers of small diameter particles are arranged on both sides of the plane. The particles are sintered into a sheet of particles that has a large core formed of large diameter particles sandwiched between two layers of small diameter particles. Similarly, a sintered stent wire can be formed by arranging large diameter particles along a first axis and then arranging small diameter particles radially outward from and coaxial to the large diameter particles. Then, the particles are sintered to form a stent wire that has a substantially porous central cavity and an outer layer that has smaller pore diameter.

In yet another embodiment, the method of forming a stent comprises arranging a sheet of solid metal between two layers of particles. The particles are then sintered to both sides of the sheet. Similarly, the particles can be sintered to one side of the metal sheet. Alternatively, particles can be oriented radially outward from a solid metal wire and sintered into a partially porous wire. The partially porous wire and the stent with a sheet metal core are believed to improve the strength of the overall stent.

According to one embodiment of the present invention, a therapeutic agent can be loaded into the pores of the stent by immersing the stent in a liquid solution containing the therapeutic agent. The stent is emersed for a period of time sufficient to permit therapeutic agent to be absorbed into the porous cavities of the stent. The therapeutic agent may be any number of drugs or chemical agents that treat arterial diseases and stent implantation side effects.

In yet another embodiment of the invention the method includes coating the stent with a polymer. The polymer may itself be loaded with one or more therapeutic agents or may be applied to delay the release of medicine or otherwise control the rate that the therapeutic agent diffuses into the body.

These and other features of the present invention will become apparent from the following more detailed description, when taken in conjunction with the accompanying drawings which illustrate, by way of example, the principles of the present invention.

BRIEF DESCRIPTION OF THE DRAWINGS

FIG. 1 is a longitudinal sectional view of a blood vessel with stent manufactured according to one embodiment of the present invention.

FIG. 2 is a porous stent wire or strut in a partially magnified, partially cut away perspective manufactured according to one embodiment of the present invention.

FIG. 3 is a magnified, cross-sectional view of unsintered packed particle.

FIG. 9 is a stent formed from a sheet of sintered metal according to one embodiment of the present invention.

FIG. 10 is a cross-sectional, partially cut away view of a sheet of sintered metal manufactured according to the principles of one embodiment of the present invention.

DETAILED DESCRIPTION OF THE PREFERRED EMBODIMENTS

Figure 5:
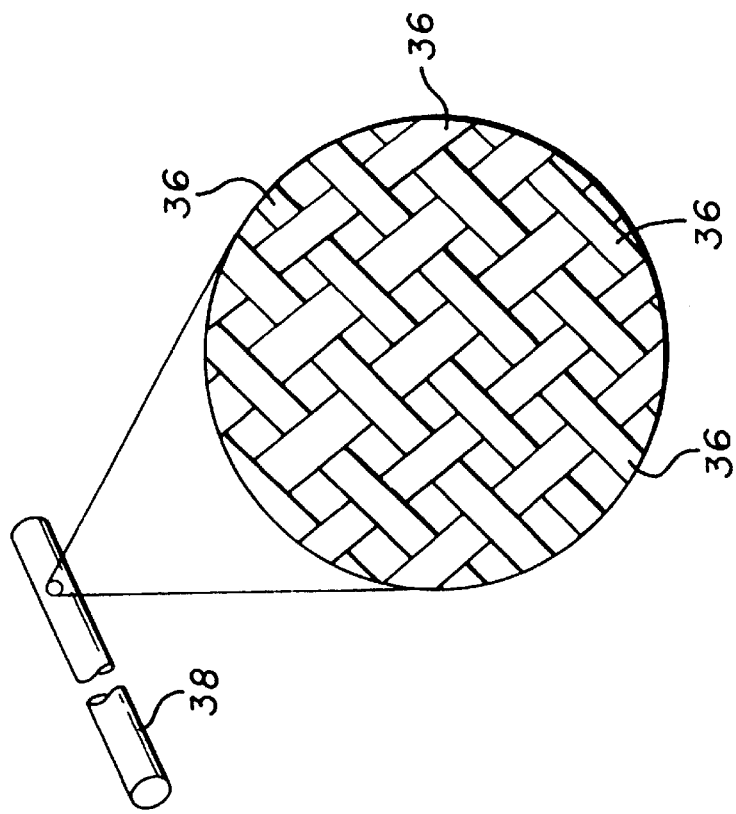
FIG. 5 is a porous stent wire or strut in partially magnified, partially cut away perspective manufactured according to one embodiment of the present invention.

Referring now to FIG. 1, the prosthesis of one embodiment is a porous stent 12 that is radially expandable against the walls 14 of a vessel 16. The stent is loaded with a therapeutic agent in the pores (18 of FIG. 2) of the stent. When placed in the vasculature, the therapeutic agent is delivered to the tissue that comes into contact with the stent. The stent of one preferred embodiment is formed of a stent wire that is porous. An example of a porous stent wire is a sintered metal wire. FIG. 2 illustrates a partial microscopic view of a sintered wire that is suitable for use in one embodiment of the present invention. The wire is porous and has several porous cavities 18. The size of the cavities preferably range between 0.01 and 20 microns in size.

Porous metal is made, according to one preferred embodiment, by the process of sintering metal. Sintering is a process of fabrication where particles are bonded together without entirely melting the particles. Particles are pressed together or molded into a desired shape. A considerable amount of pressure is first applied to press the particles together. Then, the metal is heated to temperatures slightly below the melting point of the metal. Without entirely melting, the particles bond to each other at their respective surfaces. Space remains between the lattice of the particles which define the porous cavities 18.

The formation of sintered metal is illustrated with reference to FIG. 3 and continued reference to FIG. 2. FIG. 3 is a microscopic view of a packed lattice 22 of metallic particles 24. Gaps 26 exist between each particle despite the fact that the particles are pressurized and are in contact with adjacent particles. Particles are preferably sized between 0.02 microns and 20 microns in diameter. Prior to heating, there are no chemical bonds formed between the individual particles. When the metal is heated to slightly below the melting point of the metal, the particles bond with neighboring particles. The gaps in the packed lattice form pores 18 when the particles are sintered. Thus in FIG. 2, the metal stent wire formed by the process of sintering has porous cavities 18 extending throughout the entire wire, thereby interconnecting the cavities. The cavities then can be filled with a therapeutic agent as hereinafter described. The appropriate pressure and temperature of sintering a particular metal is specific to that particular metal. One skilled in the art of metal fabrication would understand how to sinter any given metal or alloy.

For each of the embodiments, the metal stent material member can be a suitable metal such as stainless steel, tantalum, nickel-titanium alloy, platinum-iridium alloy, molybdenum-rhenium alloy, gold, magnesium, combinations thereof, although other similar materials also may be suitable. The metal can be modified to exhibit different hardnesses, and thus varying stiffnesses, by well known annealing and manufacturing processes.

One of the most important factors to be considered when making a stent according to one embodiment of the present invention is the porosity of the metal. Porosity is the total volume of pores in the sintered metal divided by the total volume of the metal. Porosity determines the amount of a therapeutic agent that can be loaded into a stent of predetermined dimensions. High porosity means that a stent can deliver more therapeutic agents or have a narrower profile because it is less dense. High porosity, according to some embodiments of the present invention, adversely affects the strength and elasticity of a metal. Consequently, there is an ongoing tradeoff between stent strength, on the one hand, and stent profile and stent load capacity on the other hand.

Pore size is a function of particle size and dimension. In one embodiment of the present invention illustrated in FIG. 3, the particles 24 are generally spherical. Size of the pore 18, particularly with generally spherical particles, is proportional to particle size. When the particles 24 have inconsistent size, smaller particles tend to fill the gaps between the larger particles. Thus, the porosity of such particles are less predictable. Consistent pore size is also important to ensure that drugs are evenly distributed throughout the stent. Consistent distribution on the other hand ensures that the tissue in contact with the stent will receive an even distribution of a therapeutic agent.

There are several types of drugs that are currently administered at the site that a stent is placed in the vessel. Examples of therapeutic drugs, or agents that can be combined with the polymeric layers include antiplatelets, antifibrin, antithrombin and antiproliferatives. Examples of anticoagulants, antiplatelets antifibrins and antithrombins include but are not limited to sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of cytostatic or antiproliferative agents include angiopeptin (a somatostatin analogue from Ibsen), angiotensin converting enzyme inhibitors such as Captopril® (available from Squibb), Cilazapril® (available from Hoffman-LaRoche), or Lisinopril® (available from Merck); calcium channel blockers (such as Nifedipine), colchicine, fibroblast growth factor (FGF) antagonists, fish oil (omega 3-fatty acid), histamine antagonists, Lovastatin® (an inhibitor of HMG-COA reductase, a cholesterol lowering drug from Merck), methotrexate, monoclonal antibodies (such as to PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon and genetically engineered epithelial cells, for example.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agent are known in the art. Furthermore, the calculation of dosages, dosage rates and appropriate duration of treatment are previously known in the art.

The therapeutic agent of one embodiment is preferably in liquid form and is loaded into a stent by immersing the stent in a medicated solution. The therapeutic agent may be dissolved in a solvent or suspended in a liquid mixture. If a suspension of drugs are used, it is important that the pore size of the stent is considerably larger than the therapeutic agent. An average pore size that is more than ten (10) times the particle size of a suspended therapeutic agent is suitable. After the stent is emersed in the medicated solution, the therapeutic agent absorbs into the pores of the stent. At which time, the loaded stent can be removed from the solution and implanted into the vasculature of a patient. Additionally, a therapeutic agent can be loaded into the stent by applying pressure to the fluid to aid the passage of medicated fluid into the porous cavities of the stent. This can be done similar to how fluid can be pressurized through the pores of a filter.

Once loaded, the therapeutic agent remains in place by the surface tension between the walls 28 of the several porous cavities 18 and the therapeutic agent. As shown in FIG. 1, the loaded or medicated stent 12 is then deployed to the site of arterial closure 13 and is expanded. The expanded stent engages the walls 14 of the vessel 16 to maintain the patency of the vessel. Once in the vessel, the therapeutic agent disseminates from the porous cavities 18, as depicted in FIG. 2, of the stent and is absorbed into the tissue of the walls of the vessel that are in contact with the stent.

The advantage of the stent of the present invention over prior art medicated stents is one of profile and strength. Metal, including sintered metal, is stronger than synthetic materials that are capable of being loaded with a therapeutic agent. Thus, in order for a medicated stent to deliver an appropriate amount of a therapeutic agent and structurally maintain vessel patency, the profile of the stent must be substantially larger than metal stents. This is true whether a metal stent is coated with a therapeutic agent, or if the stent is entirely made of a plastic material.

Sintered metal has strength and elasticity that is comparable to regular metal. Sintered metal furthermore has the added feature that it is porous. Consequently, a sintered stent can be made having a profile that is substantially comparable to a conventional metal stent. Yet, a therapeutic agent can be loaded into the pores and delivered to the site of stent implantation without the aid of medicated coatings.

Additionally, many synthetic materials, including materials that are bioabsorbable, cause inflammation of the tissue. A medicated stent that has a therapeutic agent loaded directly into the pores of the stent can avoid synthetic coatings that have been known to cause irritation at the site of stent implantation.

Figure 4:
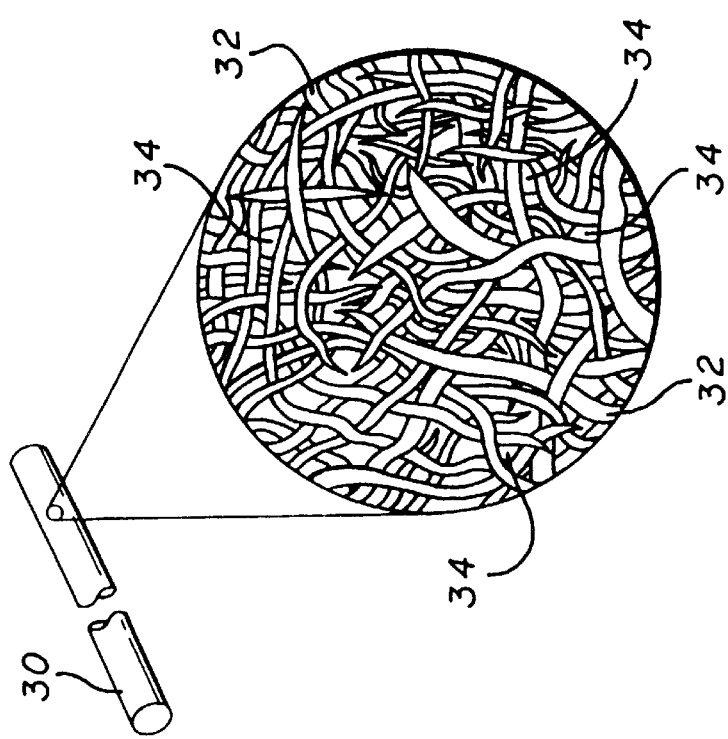
FIG. 4 is a porous stent wire or strut in partially magnified, partially cut away perspective manufactured according to one embodiment of the present invention.

FIG. 4 illustrates an alternative embodiment of a stent wire 30 constructed according to the present invention. The stent is formed of elongated particles 32, i.e., filaments and fibers. Sintered particles (24 of FIG. 2) that are generally spherical in shape are capable of forming sintered metal having a porosity in the range of 0.30 to 0.05. However, when filaments or fibers 32 are sintered, the porosity can be increased above 0.30. The technique of fabricating a stent with elongated filaments or fibers are similar to the method described above for spherical particles or powders. The filaments or fibers are molded and pressurized. Then the fibers are heated to a temperature just below the melting point of the metal.

Greater porosity of a stent made of metal filaments or fibers 32 rather than spherical particles (24 of FIG. 2) is obtained because of the irregular shape of the particles. The particles cannot be packed as tightly as regular generally spherical particles. Furthermore, the particles can be packed less densely and still maintain contact between the particles to allow sintering. Thus, the void space or pores 34 in the sintered metal are larger.

The strength of a stent wire 30 using filaments in FIG. 4 is improved because the individual strands have larger surface area to volume and contact a greater number of neighboring strands. Thus, each filament or fiber will have a larger bonding surface and may bond with a greater number of neighboring fibers. A matrix of overlapping filaments or fibers is thus formed with greater porosity and stronger inter-particle bonding.

In yet another embodiment, wire fibers 36 are woven or twined into a structure 38 as illustrated in FIG. 5. The individual strands cooperate in a synergistic manner to reinforce the strength of the wire. Additionally, the wire fibers can be woven into the form of a sintered metal sheet having improved and reinforced strength or a sintered metal tube. Other combinations of particle size and shape can be employed to form a stent wire having different characteristics.

Figure 6:
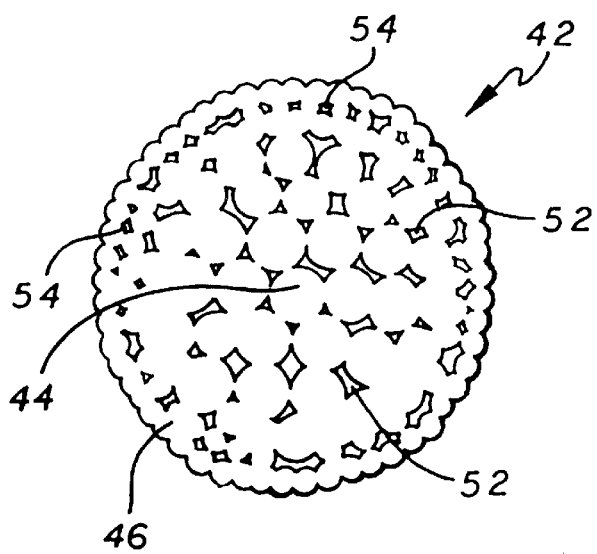
FIG. 6 is a cross-sectional view of a stent wire or strut manufactured according to one embodiment of the present invention.

In another embodiment illustrated in FIG. 6, the stent wire 42 is formed of an inner core 44 and an outer layer 41 of sintered particles. The outer layer is formed from particles having a different diameter than the diameter of the particles that form the inner core. For example, the core of the metal is formed of particles that have a diameter in the range of 10–20 microns at the core of the wire. Surrounding the core are particles that have a diameter in the range of 2–4 microns on the outer surface. The larger particles create a core having larger pores 52. This results in higher porosity and thus a higher load capacity. The smaller particles on the outer layer form smaller pores 54 which reduce the rate of diffusion of drugs into the tissue of the vessel.

When a therapeutic agent is loaded into a stent formed of the stent wire 42 illustrated in FIG. 6 a larger volume can be stored in the larger pores 52 at the core 44 of the stent wire. Once the stent is placed into the vessel, the therapeutic agent in the stent wire is delivered at a rate determined by the smaller pores 54 in the outer layer 46 of the stent wire. Such a structure is expected to have a benefit of being able to store a large amount of therapeutic agent at the core and deliver the therapeutic agent at a slower rate. Consequently, this design is desirable for low-dose, long-term drug therapy.

Figure 7:
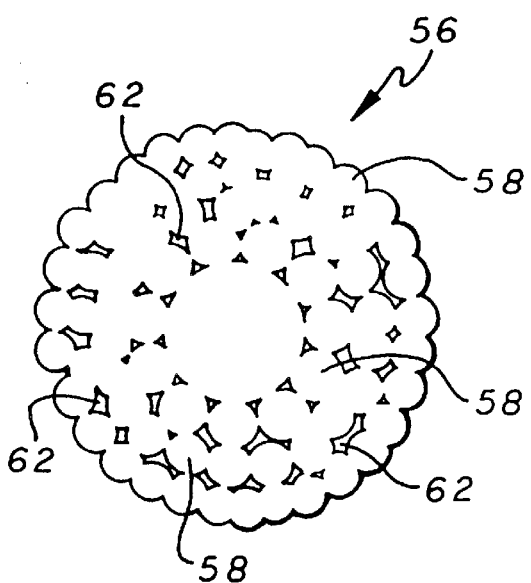
FIG. 7 is a cross-sectional view of a stent wire or strut manufactured according to one embodiment of the present invention.

Alternatively, according to another embodiment of the present invention shown in FIG. 7, a stent wire 56 is formed from sintered particles 58. The pores 62 formed between the sintered metal particle surrounding the solid core retain the therapeutic agent. The total porosity of a stent having a solid core and porous outer layer is much lower than a stent wire of similar proportion that is entirely made of sintered particles. However, the solid core reinforces the tensile strength and elasticity of the metal stent and is considerably stronger. Thus, it is desirable to use a sintered stent with a solid core for applications where maximum tensile strength and elasticity is desirable and only a relatively small amount of therapeutic agent is needed.

Figure 8:
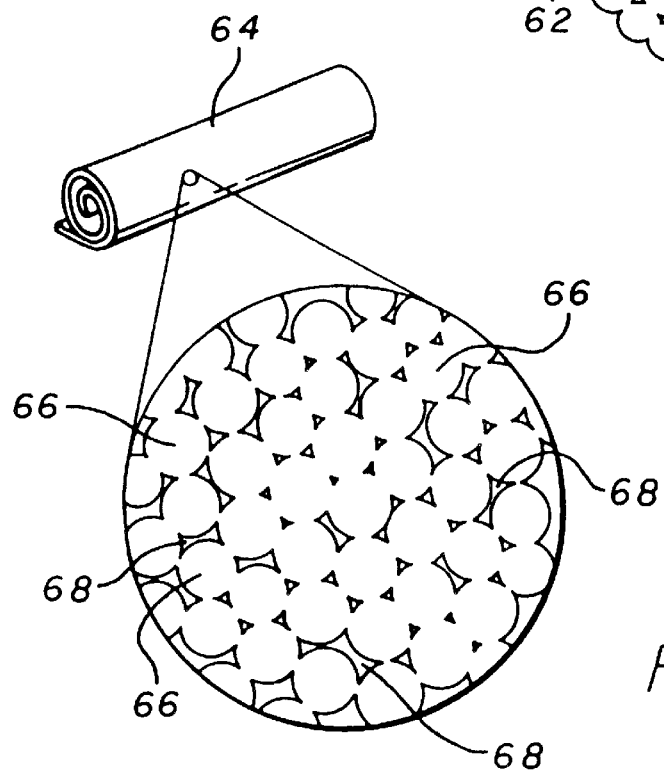
FIG. 8 is a sheet of sintered stent manufactured according to one embodiment of the present invention.

The sintered metal stent of yet another embodiment of the present invention can be made of material formed in different shapes than sintered metal. For example, the stent can be formed of a sheet of sintered metal as shown in FIG. 8 or a sintered metal tube. By way of example, metal particles 66 are arranged and pressurized into a sheet. The sheet is heated to a temperature below the melting point of the particles as described previously. The sheet of sintered metal is porous and has a plurality of pores 68.

The same principles that apply to porosity and pore size of a wire apply equally to a sintered stent that is formed into a sheet or tube. The advantage of forming the stent from a sheet of metal is that the stent is radially expandable without placing a great deal of strain on the metal lattice when it is expanded. A sheet or tube of sintered metal can be cut in the desired shape to form the metal structural member with a laser, such as a continuous $CO_2$ laser, a pulsed YAG laser, or an excimer laser, for example, or alternatively, by chemical etching or stamping. When cut from a flat sheet, the stent is then rolled into a cylindrical configuration and laser welded along the longitudinal edges.

The stent can be formed into a particular pattern known in the art for stents formed from metal sheets. One such pattern is a rolled locking design and is illustrated in FIG. 9. The sheet is etched into a stent configuration that has a head portion 72 that includes one or more slots 74 for receipt of a like number of tail portions 76. The tail portions are received into the slots so as to form a cylindrical loop. The tail end includes a plurality of teeth 78 adapted to cooperatively engage the slot of the head portion. When the teeth engage the slot, the tail is retained in place in an expanded state. Additionally, holes 80 are formed throughout the stent to reduce the metal to air ratio of the stent. The less metal in contact with the wall 14 of the vessel 16, the better the blood compatibility of the stent.

Prior to deployment, the tail end is coiled into a retracted position. The tail is threaded through the slot and wound. It is expanded by a balloon according to principles that are well known in the art for delivering and implanting a stent. As the stent is expanded by a balloon during deployment it unwinds and the teeth lock into the slots at a desired radial diameter to prevent the stent from returning to its original retracted state.

A benefit of the coiled stent shown in FIG. 9 is that the stent 70 can be etched to have a minimal surface area that comes in contact with the walls of the vessel. This may be an important feature when it is desired to cover an entire portion of the walls of a blood vessel with a therapeutic agent because the coiled sheet metal stent can be configured to maintain maximum surface area contact with the wall of the blood vessel in contrast to wire stents.

With reference to FIG. 10, another embodiment of the present invention is a sheet formed of sintered particles that are sintered to both sides 84 and 86 of a metal sheet 82. The stent of FIG. 10 is similar in structure to the stent wire of FIG. 7 that has a solid core and has porous particles sintered to the core forming a porous outer layer. The solid core reinforces the strength of the metal. The metal sheet also provides a barrier through which a therapeutic agent cannot pass. Thus, a therapeutic agent loaded into the pores 92 on the top side of 84 the sheet permeates in a first direction 88 outward from the solid core. A therapeutic agent loaded into the pores 94 on the bottom side 86 of the solid wire permeates only in a second direction 90 opposite to the direction of the therapeutic agent loaded into the pores on the top side.

When a stent as shown in FIG. 10 is looped into a cylindrical formation and placed into a vessel, only the top side 84, which is directed radially outward, engages the walls of the vessel. The bottom side 94 faces radially inward and does not come in contact with the walls of the vessel. Thus, if it is desired, a first therapeutic agent can be loaded into the top side to treat the tissue in the wall of the vessel. A second therapeutic agent can be loaded into the bottom side to prevent coagulation of the blood flowing in the vessel. Additionally, the stent can be formed so that particles are sintered only to one side of the stent. A therapeutic agent is loaded into the sintered metal on the porous side of the stent. When a stent is formed from a one-sided porous stent, it can be oriented radially outward to deliver a therapeutic agent to the tissue in the wall of the stent.

Figure 11:
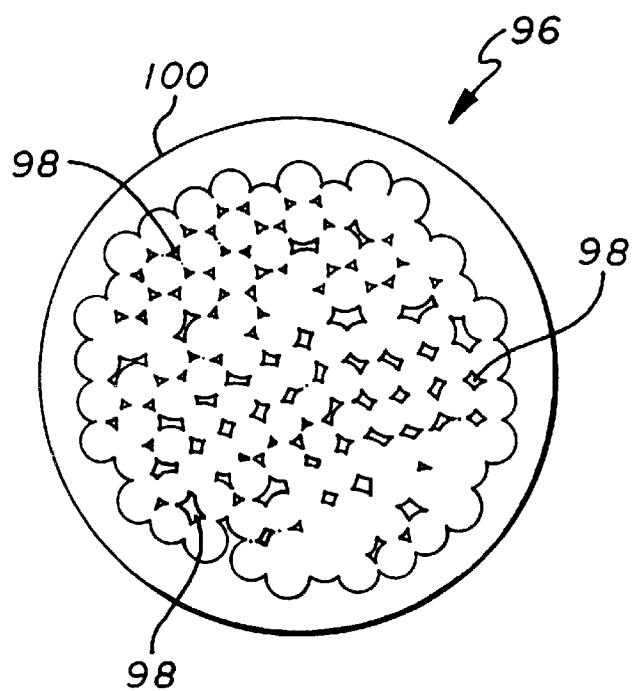
FIG. 11 is a cross-sectional view of a stent wire or strut manufactured according to the principles of one embodiment of the present invention.

FIG. 11 illustrates a cross-sectional view of a stent wire of strut according to one embodiment of the invention. The sheet has a plurality of porous cavities or pores 98. A therapeutic agent is loaded into the pores of the sintered metal. Then, a coating 100 is applied to the sintered metal. The coating may be used for several purposes as illustrated hereinafter.

Figure 12:
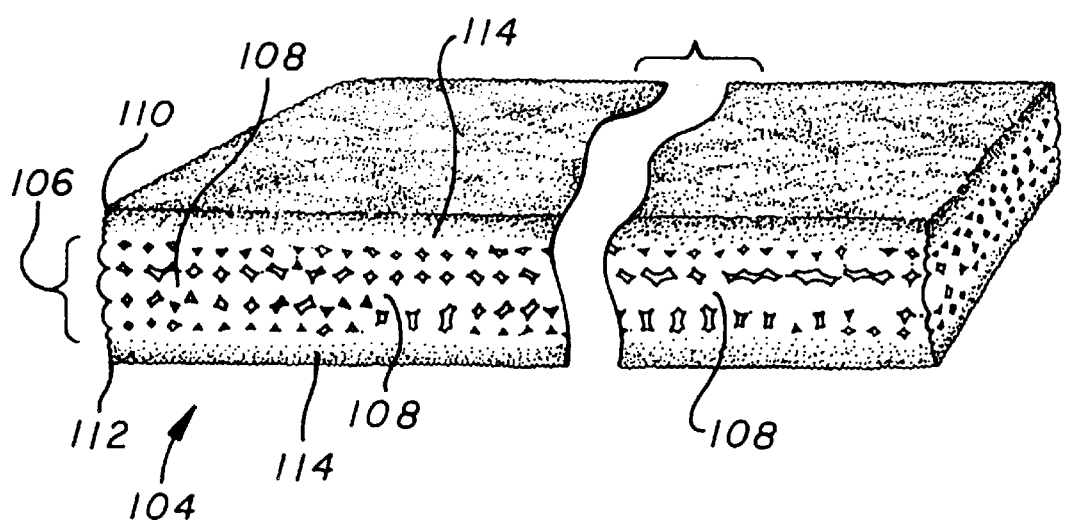
FIG. 12 is a cross-sectional view, partially cut away of a sheet of sintered metal manufactured according to the principles of one embodiment of the present invention.

With reference to FIG. 12, another embodiment of the invention is shown wherein the stent is formed of a sintered sheet 104 of metal having core 106 formed of large diameter particles 108 that form large pores. The core layer 106 is sandwiched between two layers 110 and 112 formed of smaller diameter particles 114 or particles that form smaller diameter pores. Such a sheet is formed by orienting a middle or core layer 106 of large diameter particles along a plane. A top layer of smaller diameter particles is arranged in a plane parallel to and above the middle layer. A bottom layer of particles are arranged in a plane parallel to and below the middle layer. The three layers are pressed together and sintered into a single sheet. The sheet can then be cut or etched into a stent configuration.

While one of the benefits of the present invention is to provide a stent that does not require a coating for the purpose of delivering a therapeutic agent to the blood vessel, the application of a coating after a therapeutic agent is loaded into the pores of the sintered metal does not defeat the utility of the present invention. For example, when a therapeutic agent is loaded into the pores of the stent and into a polymeric coating, the profile of the polymeric coating can be reduced. Alternatively, a larger dosage of a therapeutic agent can be delivered to the site of stent implantation. Additional benefits are observed by loading a stent with a therapeutic agent in the pores of the metal and then further applying a coating to the stent. Furthermore, even if a coating is applied to the stent, the principles of reducing profile and reinforcing the stent are still apparent because a greater volume of therapeutic agent can be delivered by a coated sintered stent than a coated, solid stent have comparable dimensions.

The polymeric material that coats a sintered metal stent of the invention preferably comprises a biodegradable, bioabsorbable polymeric film that is capable of being loaded with and capable of releasing therapeutic drugs. The polymeric coatings preferably include, but are not limited to, polycaprolactone (PCL), poly-DL-lactic acid (DL-PLA) and poly-L-lactic acid (L-PLA) or lactide. Other biodegradable, bioabsorbable polymers such as polyorthoesters, polyiminocarbonates, aliphatic polycarbonates, and polyphosphazenes may also be suitable, and other non-degradable polymers capable of carrying and delivering therapeutic drugs may also be suitable. Examples of non-degradable synthetic polymers are polyurethane, polyethylene, polyethylene teraphthalate, ethylene vinyl acetate, silicone and polyethylene oxide (PEO). The polymeric layers, according to one embodiment is to be loaded with a pharmacologic agent for use in localized drug therapy. As used in this description, the terms biodegradable, bioabsorbable, reabsorbable, degradable, and absorbable are meant to encompass materials that are broken down and gradually absorbed or eliminated by the body, whether these processes are due to hydrolysis, metabolic processes, bulk or surface erosion. In each of the foregoing embodiments, one polymeric layer is preferably about 0.0001 to 0.002 inches thick.

The thin polymeric films used to coat the stent are preferably first intermixed with the drug or drugs to be delivered, and then are typically laminated or solvent cast to the surface of the metal structural member. Lamination processing methods and temperatures can vary widely depending on the polymers used and the temperature sensitivity of the loaded drugs. Alternatively, the metal structure of the stent can be encapsulated in the layers of polymeric material by solvent casting, melt processing, insert molding, and dip coating.

In one embodiment of the present invention, the membrane is bioabsorbable, but no therapeutic agent is loaded into the polymer. The coating 100 dissolves after implantation and this delays the time that a therapeutic agent is released into the vasculature of a patient. The thickness of the coating as well as the rate at which the coating is bioabsorbed determines the length of time that the stent is mounted into the vascular before a therapeutic agent is delivered from the pores of the stent. Additionally, a therapeutic agent can be loaded into the bioabsorbable coating. Thus a therapeutic agent will be delivered to the stent at a rate determined by the bioabsorbability of the coating. Once the bioabsorbable material has completely dissolved, the therapeutic agent in the pores can be delivered at a rate determined by the pore size and porosity.

In another embodiment, it is preferred that the coating 100 is permeable and non-absorbable. In such circumstances, the rate at which the drugs permeate into the tissue is controlled by the physical properties of the particular coating selected. Additionally, the coating may be selected to reduce restenosis, thrombosis or other tissue inflammation. For example, a heparin coating is known in the art to reduce blood clotting. Heparin, when coated on a stent reduces clotting of blood on the surface of the stent. The heparin coating is affixed to the-surface of the stent through ionic bonding, end point attaching, or photo-linking the heparin.

In yet another embodiment, a first therapeutic agent is loaded into the coating and a second therapeutic agent is loaded into the pores of the stent. This may be the case when a series of drug dosages or concentrations are needed. When such a stent is placed into the vasculature, the first therapeutic agent is absorbed first by the stent and a second therapeutic agent is absorbed later by the vasculature. This variation adds a further dimension to drug treatment allowing for sequential drug therapy at the site of placement of a stent.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of manufacturing a stent for providing local delivery of a therapeutic agent at an implantation site, comprising:

sintering metallic fibers into a sintered stent material having a plurality of porous holding cavities open to one side;

forming the sintered stent material into a stent; and loading a therapeutic agent into the cavities of the stent prior to implanting the stent at the implantation site.

2. The method of claim 1, wherein said plurality of porous holding cavities extend throughout the sintered stent material.

3. The method of claim 1, futher comprising the step of weaving said metallic fibers prior to sintering the metallic fibers to form said sintered stent material.

4. The method of claim 1, wherein:

the sintered stent material comprises a sheet; and the forming step includes chemical etching the sheet into the form of an expandable stent.

5. The method of claim 2, wherein the metallic fibers are woven into a sheet prior to said sintering step.

6. The method of claim 1, wherein:

the sintered stent material comprises a sheet; and the forming step includes cutting the sheet with a laser into the form of a stent.

7. The method of claim 5, wherein the metallic fibers are woven into a sheet prior to said sintering step.

8. The method of claim 1, wherein said sintered stent material comprises a porous metal wire.

9. The method of claim 1, further comprising the step of weaving the metallic fibers into a sheet.

10. The method of claim 2, wherein the stent is emersed for a period of time sufficient to permit a therapeutic agent to be absorbed into the porous cavities of the stent.

11. The method of claim 2, wherein the stent is emersed for a period of time sufficient to permit a therapeutic agent to be absorbed into the porous cavities of the stent.

12. The method of claim 2, wherein the therapeutic agent is an anti-fibrin agent.

13. The method of claim 2, wherein the therapeutic agent is an antithrombin agent.

14. The method of claim 2, wherein the therapeutic agent is an anti-proliferative agent.

15. The method of claim 2, wherein the therapeutic agent is an anti-coagulant.

16. The method of claim 2, wherein the therapeutic agent is a $GPII_6III_a$ blocker.

17. The method of claim 2, wherein the therapeutic agent is selected from the group consisting of forskolin, aspirin, dipyridamole, coumadin, ticlopodine, and heparin.

18. The method of claim 2, wherein the therapeutic agent is a vaso-active drug.

19. The method of claim 2, wherein the therapeutic agent is an anti-inflammatory agent.

20. The method of claim 2, wherein the therapeutic agent promotes endothelialization.

21. The method of claim 2, further comprising coating the stent with a polymer.

22. The method of claim 21, wherein the coating step occurs after the loading step.

23. The method of claim 21, wherein the polymer is configured to release the therapeutic agent at a substantially constant rate.

24. The method of claim 21, wherein the polymer is a biopolymer.

25. The method of claim 21, wherein the polymer is a poly lactic acid or fibrin.

26. The method of claim 25, wherein the polymer is selected from the group consisting of polyurethane, polyethylene teraphthalate tetrafluoride, polyethylene, polyethylene oxide (PEO) and silicone.

27. The method of claim 21, wherein the polymer is a synthetic polymer.

28. The method of claim 27, wherein the polymer is a hydrogel.

29. The method of claim 21, wherein the polymer is a heparin coating.

30. The method of claim 21, wherein the polymer is mixed with the therapeutic agent.

31. The method of claim 21, wherein the polymer is degradable.

32. The method of claim 1, wherein the cavities are open on their respective one ends and the sintered stent material forms closure walls on the respective opposite ends.

33. The method of claim 1, wherein said sintered stent material forms respective cavity side walls to define the respective holding cavities, and such side walls cause such cavities to cooperate with the loaded therapeutic agent in providing surface tension for holding the therapeutic agent in the respective cavities.

34. The method of claim 1, wherein said sintered stent material comprises a plurality of layers with at least one layer configured with the cavities opening outwardly to the one side and second layer forming a closure wall closing the respective cavities from opening to the opposite side.

35. The method of claim 1, wherein said sintered stent material comprises a pair of coextensive outer layers formed with the cavities facing outwardly in opposite directions and an intermediate layer sandwiched between the outer layers.

36. The method of claim 1, wherein the cavities are of substantially uniform size.

37. The method of claim 1, wherein the cavities are of substantially irregular size.

38. The method of claim 1, wherein said sintered stent material comprises a single layer.

* * * * *

UNITED STATES PATENT AND TRADEMARK OFFICE
CERTIFICATE OF CORRECTION

PATENT NO.    : 6,240,616 B1
DATED         : June 5, 2001
INVENTOR(S)   : John Y. Yan It is certified that error appears in the above-identified patent and that said Letters Patent is hereby corrected as shown below:

<u>Title page,</u>
Item [56], U.S. PATENT DOCUMENTS, add the following:
-- 4,355,462    10/1982    MacGregor
5,571,187    11/1996    Derarathan
5,725,567     3/1998    Wolff, et al. --.

<u>Column 10,</u>
Line 17, change "2", to read -- 4 --.
Line 24, change "5", to read -- 6 --.
Lines 30-32, delete entire claim "10", and replace with the following:
-- 10. The method of claim 2, wherein the step of loading
the therapeutic agent comprises immersing the stent in a
liquid solution containing the therapeutic agent. --.
Line 64, change "21", to read -- 24 --.

Signed and Sealed this

Twenty-sixth Day of November, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,240,616 B1  Page 1 of 1
DATED : June 5, 2001
INVENTOR(S) : John Y. Yan It is certified that error appears in the above-identified patent and that said Letters Patent is hereby corrected as shown below:

Column 2,
Line 39, change "emersed" to -- immersed. --

Column 10,
Line 32, change "emersed" to -- immersed. --

Signed and Sealed this

Eleventh Day of February, 2003

JAMES E. ROGAN
*Director of the United States Patent and Trademark Office*